United States Patent [19]

Hara et al.

[11] 4,241,155
[45] Dec. 23, 1980

[54] METHOD FOR STABILIZING ORGANIC SUBSTRATES INCLUDING PHOTOGRAPHIC DYE IMAGES AGAINST LIGHT

[75] Inventors: Hiroshi Hara, Asaka; Kotaro Nakamura, Minami-ashigara; Yoshiaki Suzuki, Minami-ashigara; Shigeru Oono, Minami-ashigara, all of Japan

[73] Assignee: Fuji Photo Film Co., Ltd., Minami-ashigara, Japan

[21] Appl. No.: 960,545

[22] Filed: Nov. 14, 1978

[30] Foreign Application Priority Data

Nov. 15, 1977 [JP] Japan .................. 52-137027

[51] Int. Cl.$^3$ .............................................. G03C 7/00
[52] U.S. Cl. ..................................... 430/17; 430/216; 430/372; 430/384; 430/386; 430/388; 430/390; 430/551; 430/559; 430/958; 260/429 R; 260/439 R
[58] Field of Search ............... 96/56, 67, 74, 84 R, 96/66.4, 109, 110, 114.5, 119, 99; 252/300 R; 260/429 R, 429 C, 429 J, 438.1, 439 R

[56] References Cited

U.S. PATENT DOCUMENTS

| | | | |
|---|---|---|---|
| 2,976,122 | 3/1961 | Ertelt et al. | 260/429 R |
| 3,293,208 | 12/1966 | Milionis et al. | 260/439 R |
| 3,588,216 | 6/1971 | Bloom | 260/429 R |
| 3,885,966 | 5/1975 | Gracia et al. | 96/94 R |
| 4,050,938 | 9/1977 | Smith, Jr. et al. | 96/84 UV |
| 4,076,531 | 2/1978 | Crowell | 96/94 R |

OTHER PUBLICATIONS

Photographic Gelatin, Croome et al., Focal Press, N.Y. ©1965, pp. 76-83.
Stabilization of Photographic Silver Halide Emulsions, Birr, Focal Press ©1974, pp. 28-35, 115-117.
Photographic Emulsions, James, NDC, Park Ridge, N.J. ©1973, pp. 24 to 27.
Mechanism of Oxid. Photodegradation and of UV Stabilization of Polyolefins, Cicchetti, Adv. Polymer Sci. vol. 7, pp. 70-112, (1970).

*Primary Examiner*—J. Travis Brown
*Attorney, Agent, or Firm*—Sughrue, Rothwell, Mion, Zinn and Macpeak

[57] ABSTRACT

A method for stabilizing an organic substrate to light the substrate having an absorption maximum in the range of about 300 nm–about 800 nm, which comprises making at least one complex represented by following general formula (I) coexist with the substrate:

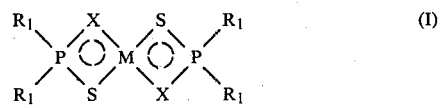

wherein M represents an atom selected from the group consisting of Cu, Co, Ni, Pd and Pt, X represents O or S, $R_1$ represents an alkyl group, an aryl group, an alkoxy group, an aryloxy group or, when taken together, the $R_1$'s bound to the same phosphorus atom represent the non-metallic atoms necessary to complete a 6-membered ring together with the phosphorus atom. A photographic element containing the above complex is also claimed.

23 Claims, No Drawings

METHOD FOR STABILIZING ORGANIC SUBSTRATES INCLUDING PHOTOGRAPHIC DYE IMAGES AGAINST LIGHT

BACKGROUND OF INVENTION

1. Field of Invention:

This invention relates to stabilization of an organic substrate against light and, more particularly, it is concerned with stabilization of organic compounds, in particular organic dyes, against light.

2. Discussion of the State of the Art:

In general, it is well known that organic substrates such as organic dyes tend to undergo color deterioration or discoloration. In the field of inks, fiber-dyeing or color photography, numerous investigations have been conducted to prevent such color deterioration or discoloration of organic dyes by light, or to improve their light fastness. The present invention can be used to a great advantage for improving the light fastness of the above-described organic substrates.

The term "organic substrate material" or "organic substrate" as they are used in this specification include not only materials which appear to be colored or colorless to the human eye under sunlight, but also include materials having an absorption maximum in the visible region such as optically brightening agents, and materials having an absorption maximum in the infrared region. In the present invention, organic substrates include organic compounds having an absorption maximum in the range of from about 300 nm in ultraviolet region to about 800 nm in infrared region.

The present invention is particularly directed to improving the light fastness of organic substrate materials occurring in photographic materials, e.g., color films, prints, etc., in colored polymers useful as agricultural vinyl cover sheets, umbrellas, tents, etc.; of fluorescent whitening agents; and dyed textiles, etc.

The term "dye" or "dyestuff" as used in this specification includes organic materials appearing colored to the human eye under sunlight.

The term "light" as used herein means electromagnetic radiation of wavelength less than about 800 nm, and includes ultraviolet rays of less than about 400 nm, visible light waves of about 400 nm to about 700 nm, and infrared rays of about 700 nm to about 800 nm.

Organic substrates such as dyes or dyestuffs tend to suffer color deterioration or discoloration when exposed to light, and there have been many reported methods for reducing the color failure or discoloration, or methods for improving the light fastness of the substrates. For example, U.S. Pat. No. 3,432,300 describes that light fastness of such organic compounds as indophenol, indoaniline, azo and azomethine dyes against visible and ultraviolet light can be improved by mixing them with a phenol type compound having a fused hetero ring system.

In the field of silver halide photographic light-sensitive materials, azomethine dyes or indoaniline dyes are generally formed through the reaction between an oxidation product of an aromatic primary amine developing agent and a color former or color coupler as described in G. E. K. Mees and T. H. James; The Theory of the Photographic Process (published by Macmillan Co. in 1967), chap. 17. Many methods have been known for improving the stability of the images made by these dyes, or color images, against light. For example, quinone derivatives have been used as described in U.S. Pat. Nos. 2,360,290, 2,418,613, 2,675,314, 2,701,197, 2,704,713, 2,728,659, 2,732,300, 2,735,765, 2,710,801, 2,816,028, British Pat. No. 1,363,921, etc., gallic acid derivatives described in U.S. Pat. Nos. 3,457,079, 3,069,262, Japanese Patent Publication No. 13,496/68, etc., p-alkoxyphenols described in U.S. Pat. Nos. 2,735,765 and 3,698,909, and chroman or coumaran derivatives described in U.S. Pat. Nos. 3,432,300, 3,573,050, 3,574,627, 3,764,337, 3,574,626, 3,698,909, 4,015,990, etc. However, these compounds are not satisfactory, though they show the effect of preventing color failure or discoloration of color images to some extent.

Also, British Pat. No. 1,451,000 describes the method for improving stability of organic substrates against light by using azomethine quenching compounds having an absorption maximum in a more bathochromic region than that of the base compounds. However, this method is disadvantageous because the azomethine quenching compounds themselves are strongly colored and they exert detrimental influences on the hue of the base material.

In addition, the use of metal complexes for preventing photo deterioration of polymers is described in *J. Polym. Sci.*, Polym. Chem. Ed., 12, 993 (1974) by J. P. Guillory and R. S. Becker, and in *J. Polym. Sci.*, Polym. Let. Ed., 13, 71 (1975) by R. P. R. Ranameera and G. Scoot. Further, methods of stabilizing dyes with metal complexes are described in Japanese Patent Application (OPI) No. 87,649/75 (The term "OPI" as used herein refers to a "published unexamined Japanese patent application".) and Research Disclosure 15162 (1976). However, these complexes do not have a large effect and, in addition, they are not sufficiently soluble in organic solvents such that they can be dissolved in a high enough amount to obtain the fullest color deterioration prevention. Further, these complexes are themselves strongly colored, they adversely affect the hue and purity and organic substrates, in particular dyes, when added in a large amounts.

SUMMARY OF THE INVENTION

It is therefore an object of the present invention to provide a method for improving stability of organic substrates against light.

Another object of the present invention is to provide a method of improving the stability of organic substrates and, in particular, dyes or dyestuffs, against light without deteriorating their color hue and purity.

A further object of the present invention is to provide a method of improving the stability of organic substrates against light using an organic base material-stabilizing agent having a high solubility in organic solvents and a high miscibility with the organic substrates.

Still a further object of the present invention is to provide a method of improving the stability of a color dye forming a color photographic image to light.

Still a further object of the present invention is to provide a method for improving the stability of a dye formed by the reaction between an aromatic primary amine developing agent and a color coupler to light.

Other objects of the present invention will become apparent from the following description of the invention.

DESCRIPTION OF THE INVENTION

The above-described and other objects of the present invention have been attained by allowing at least one compound represented by general formula (I) to coexist with an organic substrate having an absorption maximum in the range of from about 300 nm to about 800 nm:

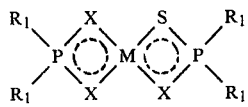

wherein M represents an atom selected from the group consisting of Cu, Co, Ni, Pd and Pt, X represents O or S, $R_1$ represents an alkyl group, an aryl group, an alkoxy group, an aryloxy group or, when taken together, the $R_1$'s bound to the same phosphorus atom represent the non-metallic atoms necessary to completing a 6-membered heterocyclic ring with phosphorus atom.

The terms "in the presence of" or "coexistant with" as used in the specification refer not only to co-existence of the substrate material and the compound of the formula (I) in the same solution, dispersion, emulsion or layer but also to the existence of the organic substrate and the complex in adjacent layers of a multi-layered photographic material. As long as the complex compound is associated with the organic substrate material such that it improves the light fastness of the organic substrate, it is used "in the presence of" or "coexists" with the substrate for purposes of the present invention.

Alkyl groups represented by $R_1$ include substituted and unsubstituted and straight or branched chain alkyl groups. As such alkyl groups, those having 1 to 20 carbon atoms (excluding the carbon atoms in any substituent moiety) are preferred. Specific examples of the alkyl group are, for example, a methyl group, an ethyl group, an n-propyl group, an iso-propyl group, an n-butyl group, an n-amyl group, an iso-amyl group, an n-decyl group, an n-octadecyl group, etc.

Aryl groups represented by $R_1$ include both substituted and unsubstituted, monocyclic or bicyclic aryl groups, and those having 6 to 14 carbon atoms (excluding the carbon atoms in any substituent moiety) are preferred. Specific examples are, for example, a phenyl group and a naphthyl group.

Alkoxy groups represented by $R_1$ include both substituted and unsubstituted alkoxy groups, the alkyl moiety of which may be straight, branched or cyclic, with alkyl moieties containing 1 to 20 carbon atoms (excluding carbon atoms in any substituent moiety) being preferred. Specific examples of the alkoxy group are, for example, a methoxy group, an ethoxy group, an n-propoxy group, an iso-propoxy group, an n-butoxy group, an n-hexadecyloxy group, a cyclohexyloxy group, etc.

Aryloxy groups represented by $R_1$ include both substituted and unsubstituted, monocyclic and bicyclic aryloxy groups, and those having 6 to 14 carbon atoms (excluding carbon atoms in any substituent moiety) are preferred. Specific examples thereof are, for example, a phenoxy group and a naphthyloxy group.

As the 6-membered ring formed by any two $R_1$'s bound to the same phosphorus atom in general formula (I), those which contain 3 to 5 carbon atoms (excluding the carbon atoms in any substituent moiety) are preferred. Specific examples thereof include, for example, a 1,3-dioxo-2-phosphacyclohexane ring.

As the examples of the substituents for the alkyl group, the aryl group, the alkoxy group, the aryloxy group, represented by $R_1$, and the 6-membered ring formed by any two $R_1$'s bound to the same phosphorus atom, there are illustrated, for example, a halogen atom (e.g., a chlorine atom, a bromine atom or a fluorine atom), a cyano group, a substituted or unsubstituted straight or branched alkyl group containing 1–20 carbon atoms (e.g., a methyl group, an ethyl group, an n-propyl group, an i-propyl group, an n-butyl group, a t-butyl group, an n-hexyl group, a t-octyl group, an n-decyl group, an n-dodecyl group, an n-tetradecyl group, an n-heptadecyl group, an n-octadecyl group or a methoxyethoxyethyl group, etc.), a substituted or unsubstituted, monocyclic or bicyclic aryl group (e.g., a phenyl group, a naphthyl group, an anisyl group, etc.), a substituted or unsubstituted branched or straight chain alkoxy group (e.g., a methoxy group, an ethoxy group, a butoxy group, a propoxy group, a methoxyethoxy group, etc.), a substituted or unsubstituted monocyclic or bicyclic aryloxy group (e.g., a phenoxy group, a tolyloxy group, a naphthoxy group, a methoxyphenoxy group, etc.), a substituted or unsubstituted alkoxycarbonyl group (e.g., a methoxycarbonyl group, a butoxycarbonyl group, a phenoxymethoxycarbonyl group, etc.), a substituted or unsubstituted aryloxycarbonyl group (e.g., a phenoxycarbonyl group, a tolyloxycarbonyl group, a methoxyphenoxycarbonyl group, etc.), a substituted or unsubstituted acyl group (e.g., a formyl group, an acetyl group, a valeryl group, a stearoyl group, a benzoyl group, a toluoyl group, a naphthoyl group, a p-methoxybenzoyl group, etc.), a substituted or unsubstituted acyloxy group (e.g., an acetoxy group, a benzoyloxy group, etc.), a substituted or unsubstituted acylamino group (e.g., an acetamido group, a benzoylamido group, a methoxyacetamido group, etc.), a substituted or unsubstituted alkyl or aryl carbamoyl group (e.g., an N-butylcarbamoyl group, an N,N-diethylcarbamoyl group, an N-(4-methoxy-n-butyl)carbamoyl group, etc.), a substituted or unsubstituted alkyl or aryl sulfamoyl group (e.g., an N-butylsulfamoyl group, an N,N-diethylsulfamoyl group, an N-dodecylsulfamoyl group, an N-(4-methoxy-n-butyl)sulfamoyl group, etc.), a substituted or unsubstituted alkyl or aryl sulfonylamino group (e.g., a methylsulfonylamino group, a phenylsulfonylamino group, a methoxymethylsulfonylamino group, etc.), and a substituted or unsubstituted alkyl or aryl sulfonyl group (e.g., a mesyl group, a tosyl group, a methoxymethanesulfonyl group, etc.). In the foregoing substituents and throughout this specification, any alkyl moiety preferably contains 6 to 20 carbon atoms and any aryl moiety contains 6 to 14 carbon atoms. Furthermore, the alkyl moieties may be straight or branched chain and the aryl monocyclic or bicyclic.

Of the compounds represented by general formula (I), compounds represented by following general formula (Ia) are preferably used in accordance with the present invention:

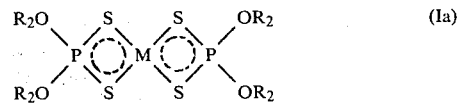

wherein M represents an atom selected from the group consisting of Cu, Co, Ni, Pd and Pt, and $R_2$ represents an alkyl group containing 1 to 20 carbon atoms or an aryl group containing 6 to 14 carbon atoms.

The alkyl group represented by $R_2$ may be straight or branched, and preferably contains 1 to 20 carbon atoms excluding the carbon atoms in any substituent moiety. Specific examples of the alkyl group include, for example, a methyl group, an ethyl group, a n-propyl group, an iso-propyl group, a n-butyl group, a n-amyl group, an iso-amyl group, a n-decyl group, a n-octadecyl group, etc.

The aryl group represented by $R_2$ preferably contains 6 to 14 carbon atoms excluding the carbon atoms in any substituent moiety and is monocyclic or bicyclic. As the specific examples thereof, there are illustrated, for example, a phenyl group and a naphthyl group.

As the substituents for the alkyl group or aryl group represented by $R_2$, the substituents disclosed for $R_1$ above are preferably used.

The following structural formulae represent metal complexes falling within the scope of aforesaid general formula (I), which are particularly effective for the practice of the present invention. However, the present invention is not to be construed as in any way being limited to these compounds.

| Compound | M | X | $R_1$ |
|---|---|---|---|
| I-1 | Ni | O | $C_2H_5O$ |
| I-2 | Ni | S | $CH_3$ |
| I-3 | Ni | S | $CH_3O$ |
| I-4 | Ni | S | $C_2H_5O$ |
| I-5 | Ni | S | $nC_3H_7O$ |
| I-6 | Ni | S | $iC_3H_7O$ |
| I-7 | Ni | S | $nC_4H_9O$ |
| I-8 | Ni | S | $iC_4H_9O$ |
| I-9 | Ni | S | 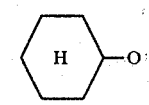 |
| I-10 | Ni | S | $nC_6H_{13}O$ |
| I-11 | Ni | S | $nC_{12}H_{25}O$ |
| I-12 | Ni | S | $nC_{16}H_{33}O$ |
| I-13 | Ni | S | $Cl(CH_2)_6O$ |
| I-14 | Ni | S | $CH_3O(CH_2)_2O$ |
| I-15 | Ni | S | $nC_4H_9O(CH_2)_2O(CH_2)_2O$ |
| I-16 | Ni | S | $C_6H_5(CH_2)_2O$ |
| I-17 | Ni | S | 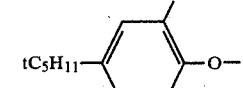 |
| I-18 | Ni | S | $C_6H_5CO_2(CH_2)_{10}O$ |
| I-19 | Ni | S | $C_6H_5SO_2(CH_2)_{10}O$ |
| I-20 | Ni | S | $C_6H_5O$ |
| I-21 | Ni | S | $mC_{15}H_{31}-C_6H_4O$ |
| I-22 | Ni | S | $C_6H_5CONH(CH_2)_5O$ |
| I-23 | Ni | S | $p-CH_3C_6H_4SO_2NH(CH_2)_5O$ |
| I-24 | Ni | S | $CH_3CONH(CH_2)_2O$ |
| I-25 | Ni | S | $CH_3CO(CH_2)_3O$ |
| I-26 | Cu | S | $C_2H_5O$ |
| I-27 | Co | S | $C_2H_5O$ |
| I-28 | Pd | S | $C_2H_5O$ |
| I-29 | Pt | S | $C_2H_5O$ |

Compound
I-30

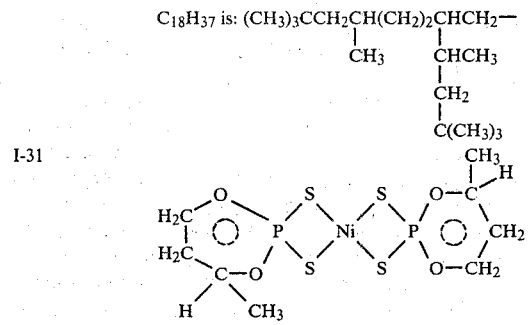

wherein $C_{18}H_{37}$ is: $(CH_3)_3CCH_2CH(CH_2)_2CHCH_2-$
with branches $CH_3$ and $CHCH_3$, $CH_2$, $C(CH_3)_3$

I-31

[Structure of I-31 complex with Ni center]

General processes for synthesizing the above-described complexes are described in, for example, C. K. Jørgensen; Inorg. Nucl. Chem. 24, 1571 (1962) and J. D. Lebedda, R. A. Palmer; Inorg. Chem. 11, 484 (1972).

A solution of $P_2S_5$ and an alcohol ($R_1OH$ wherein $R_1$ has the same meaning as defined above; 1:4.5 in a molar ratio) in benzene is refluxed for 1 hr. To the solution is added 1 mol of metal chloride such as $NiCl_2·6H_2O$. The mixture is again refluxed for 1 hr. After filtering, the solvent is evaporated off and the resulting crystals are collected in a conventional manner. If required, recrystallization is performed from a benzene-ethanol solvent mixture.

SYNTHESIS EXAMPLE 1

Synthesis of compound I-12

15 g of $P_2S_5$ and 74 g of n-hexadecyl alcohol were added to 100 ml of benzene and refluxed for 1 hour with stirring. To this solution was added 21 g of $NiCl_2·6H_2O$, and the reflux was continued for 1 hour under stirring. After hot filtration, the filtrate was allowed to cool. The crystals which formed were filtered out and washed with ethanol, followed by recrystallizing from benzene/ethanol to yield 60 g of compound I-12.

SYNTHESIS EXAMPLE 2

Synthesis of compound I-18

15 g of $P_2S_5$ and 85 g of 2-(2,4-di-t-amylphenoxy)-ethanol were added to 100 ml of benzene and refluxed for 7 hours under stirring. To this solution was added 22 g of $NiCl_2·6H_2O$, and the reflux was continued for 3 hours under stirring.

This solution was hot filtered, and the filtrate was concentrated and purified through liquid column chromatography (silica gel) to yield 80 g of compound I-18.

In a manner analogous to the syntheses illustrated above, the other chelates of formula I can be prepared. The chelate compound used in the present invention is effective for improving the light fastness of a wide variety of organic substrate materials as will be apparent from their extensive discussion below. The exact chemical nature of the substrate is not critical as long as the substrate has an absorption maximum in the range of 300 nm to 800 nm.

The organic substrates which can be treated in accordance with the present invention include all dyes belonging to the groups classified based on dyeing properties. In other words, dyes such as water-soluble dyes (e.g., basic dyes, acidic dyes, direct cotton dyes, solubilized vat dyes, mordant dyes, etc.), water-insoluble dyes (e.g., sulfur dyes, vat dyes, oil-soluble dyes, disperse dyes, azoic dyes, oxidation dyes, etc.), and reactive dyes. These organic substrates not only include dyes appearing colored to the human eye under sunlight but colorless or slightly yellow fluorescent brightening dyes as well.

Of these substrates, dyes belonging to the chemical category of quinoneimine dyes (e.g., azine dyes, oxazine dyes, thiazine dyes, etc.), methine and polymethine dyes (e.g., cyanine dyes, azomethine dyes, etc.), azo dyes, anthraquinone dyes, indoamine and indophenol dyes, indigoid dyes, carbonium dyes, formazane dyes, etc. are preferably the subject of the present invention.

The organic substrates of the present invention include the image-forming dyes used in the field of photography, such as dyes produced from color couplers, DRR (dye releasing redox) compounds, DDR (diffusible dye releasing) couplers, amidrazone compound dyes, developing agents, etc. and dyes for use in a silver dye-bleaching process.

Dyes preferably used in the present invention as the organic substrates are anthraquinone dyes, quinoneimine dyes, azo dyes, methine dyes, polymethine dyes, indoamine dyes, indophenol dyes and formazan dyes. Dyes most preferably used in the practice of the present invention are methine and polymethine dyes, and indoamine and indophenol dyes. The methine and polymethine dyes and the indoamine and indophenol dyes include compounds containing the following moiety:

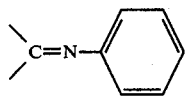

wherein the phenyl group may be substituted by, for example, an alkyl group, an alkoxy group, a halogen atom, an amino group, or the like.

The dye-forming couplers suitable for use with the present invention include yellow, magenta and cyan dye-forming type couplers. These couplers may be the so-called 4-equivalent or 2-equivalent type couplers as described in, e.g., U.S. Pat. Nos. 3,277,155 and 3,458,315.

Yellow dye-forming couplers generally contain a methylene group activated by at least one carbonyl group (for example, open chain ketomethylene groups), and include beta-diketones and beta-ketoacylamides such as benzoyl acetanilide, and α-pivalyl acetanilide. Suitable couplers are described in, for example, U.S. Pat. Nos. 2,428,054, 4,026,706, 2,499,966, 2,453,661, 2,778,658, 2,908,573, 3,227,550, 3,253,924, 3,277,155, 3,384,657, British Pat. No. 503,752, etc.

Magenta dye-forming couplers such as 5-pyrazolone type couplers can also be used in the present invention. Couplers of this type are described in, for example, U.S. Pat. Nos. 2,600,788, 2,725,292, 2,908,573, 3,006,759, 3,062,653, 3,152,896, 3,227,550, 3,252,924, 4,026,706, 3,311,476, etc.

Other magenta dye-forming couplers are indazolones of the type described in Vittum and Weissberger; "Journal of Photographic Science", Vol. 6, p. 158 et seq. (1958), pyrazolinobenzimidazoles described in, for example, U.S. Pat. No. 3,061,432, pyrazolo-s-triazoles described in Belg. Pat. No. 724,427, and 2-cyanoacetyl coumaron described in, for example, U.S. Pat. No. 2,115,394.

Cyan dye-forming couplers to be used in the present invention include phenolic and α-naphtholic compounds. Compounds of this type are described in U.S. Pat. Nos. 2,275,292, 2,423,730, 2,474,293, 2,895,826, 2,908,573, 3,043,892, 4,026,706, 3,227,550 and 3,253,294.

Such couplers are further described in, for example, Kirk-Othmer's Encyclopedia of Chemical Technology, vol. 5, pp. 822–825 and Glafkides's Photographic Chemistry, vol. 2, pp. 596–614.

As has been described above, dyes formed upon the reaction between an oxidized aromatic primary amine silver halide-developing agent and a color couplers can be used in conjunction with the present invention.

The above-described developing agents include aminophenols and phenylenediamines, which may be used alone or in combination. Typical examples of developing agents capable of producing organic substrates upon coupling with various color couplers include:

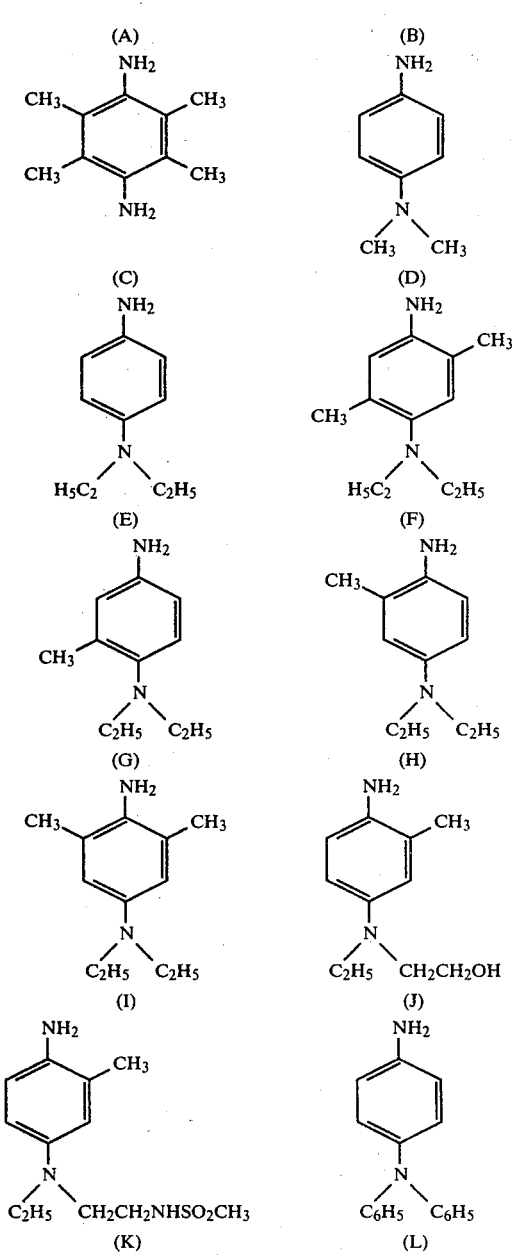

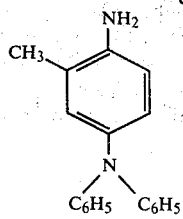 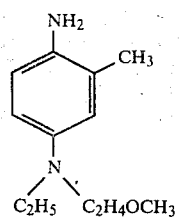

The developing agents illustrated above and others can provide organic substrates upon the reaction with photographic color couplers. Cyan, Magenta and Yellow Couplers which are preferably employed are represented by the formulae (IIa), (IIb) or (IIc) below respectively:

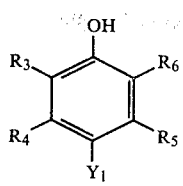 (IIa)

wherein $R_3$, $R_4$, $R_5$ and $R_6$ each repesents a hydrogen atom, a halogen atom (e.g., fluorine, chlorine, bromine or iodine), an alkyl group having 1 to 20 carbon atoms (hereinafter, all of the alkyl groups referred to with respect of formulae (IIa), (IIb) and (IIc) may possess 1 to 20 carbon atoms) (e.g., methyl, ethyl, octyl, dodecyl, tetradecyl, octadecyl, etc.); an alkyl- or aryl-substituted carbamoyl wherein the aryl moiety has 6 to 10 carbon atoms, (hereinafter all of the aryl groups referred to with respect to formulae (IIa), (IIb) and (IIc) may possess 6 to 10 carbon atoms) (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R_3$ and $R_4$ may combine with each other to form a six-membered carbocyclic ring (e.g., a benzene ring which may further be substituted with an alkyl or aryl group).

$Y_1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an amino-sulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R_3$, $R_4$, $R_5$ and $R_6$, or the 6-membered ring formed by combining $R_3$ and $R_4$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di(t)-amylphenoxy, etc.); a halogen atom (e.g., chlorine, bromine, fluorine, etc.); and the like.

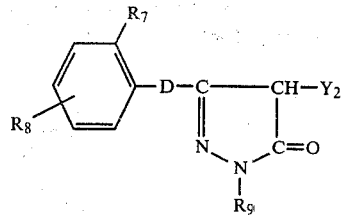 (IIb)

wherein $R_7$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R_8$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc. and $R_9$ represents an aryl group (e.g., phenyl, naphthyl, etc.) said alkyl and aryl groups having the number of carbon atoms discussed above with respect to formula (IIa).

D represents an amino group, a carbonylamino group, or a ureido group.

$Y_2$ represents a hydrogen atom, a halogen atom (e.g., chlorine, bromine, etc.); or a group which is releasable upon reaction with the oxidation product with a developing agent (e.g., an arylazo group, an aryloxy group, an acyloxy group, an alkylthio group, an arylthio group, etc.). Such groups are well known.

The alkyl or alkoxy group represented by $R_7$, the alkyl, amido, N-alkylcarbamoyl, N-alkylsulfamoyl, alkoxycarbonyl or acyloxy group represented by $R_8$, or the aryl group represented by $R_9$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

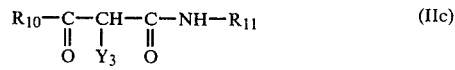 (IIc)

wherein $R_{10}$ represents an alkyl group (e.g., methyl, ethyl, (t)-butyl, (t)-octyl, etc.) or an aryl group (e.g., phenyl) and $R_{11}$ represents an aryl group (e.g., phenyl).

$Y_3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R_{10}$ and the aryl group represented by $R_{11}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc.

As the examples of couplers capable of reacting with the above-described or other developing agents to form organic substrates, there are illustrated the following:

C-1

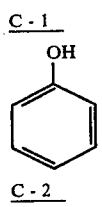

C-2

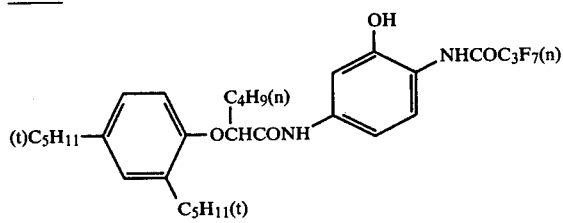

C-3

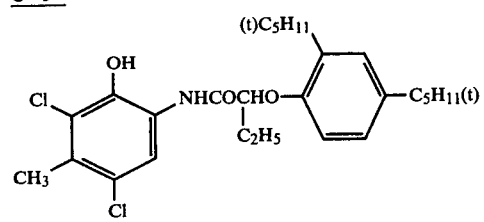

C-4

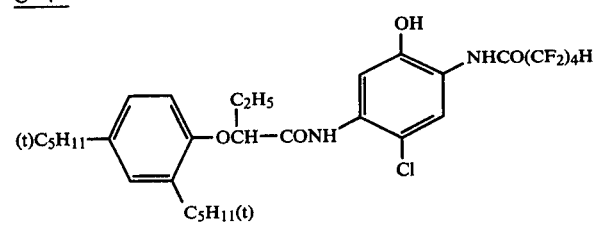

C-5

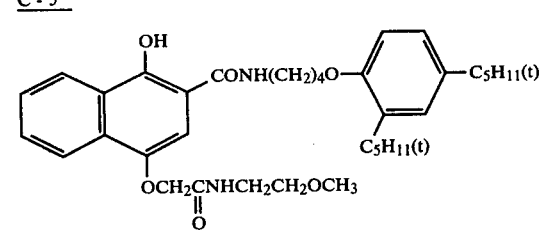

C-6

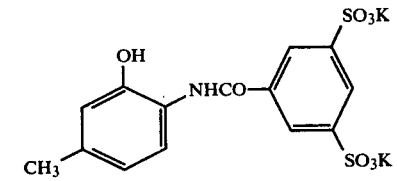

C-7

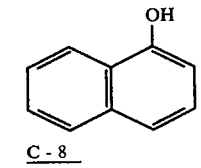

C-8

-continued
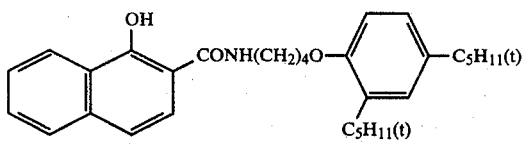
C - 9
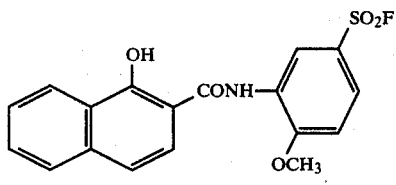
C - 10
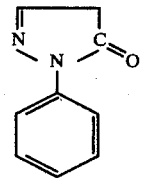
C - 11
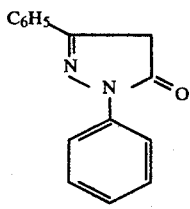
C - 12
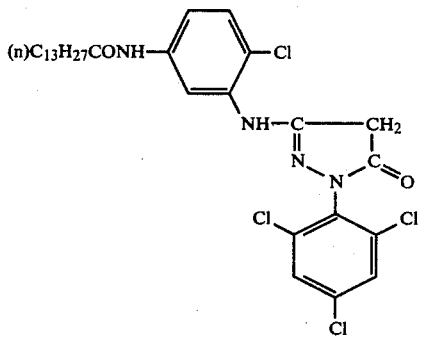
C - 13
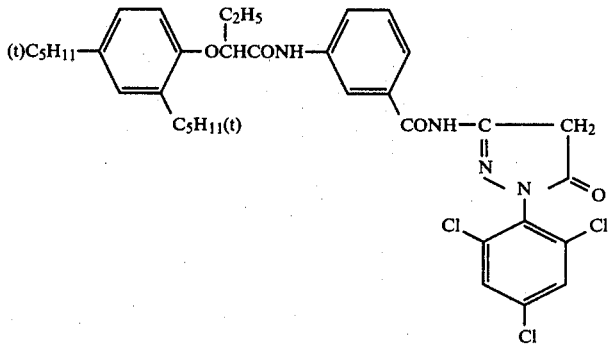
C - 14

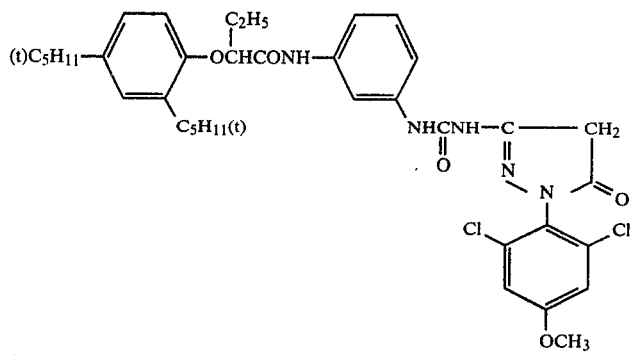
C - 15
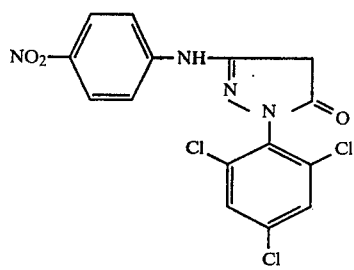
C - 16
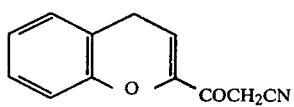
C - 17
CN—CH₂—CN
C - 18
C - 19
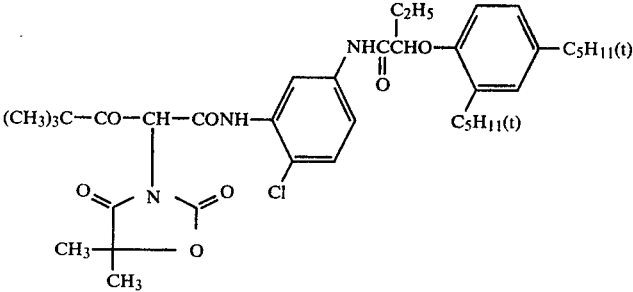
C - 20
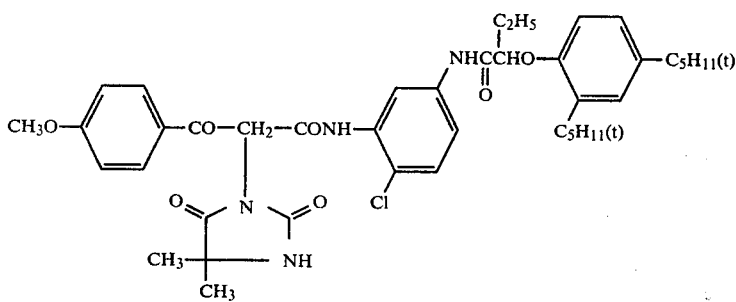
As the examples of other dyes which may be used as substrates in the practice of the present invention, there are illustrated the following:

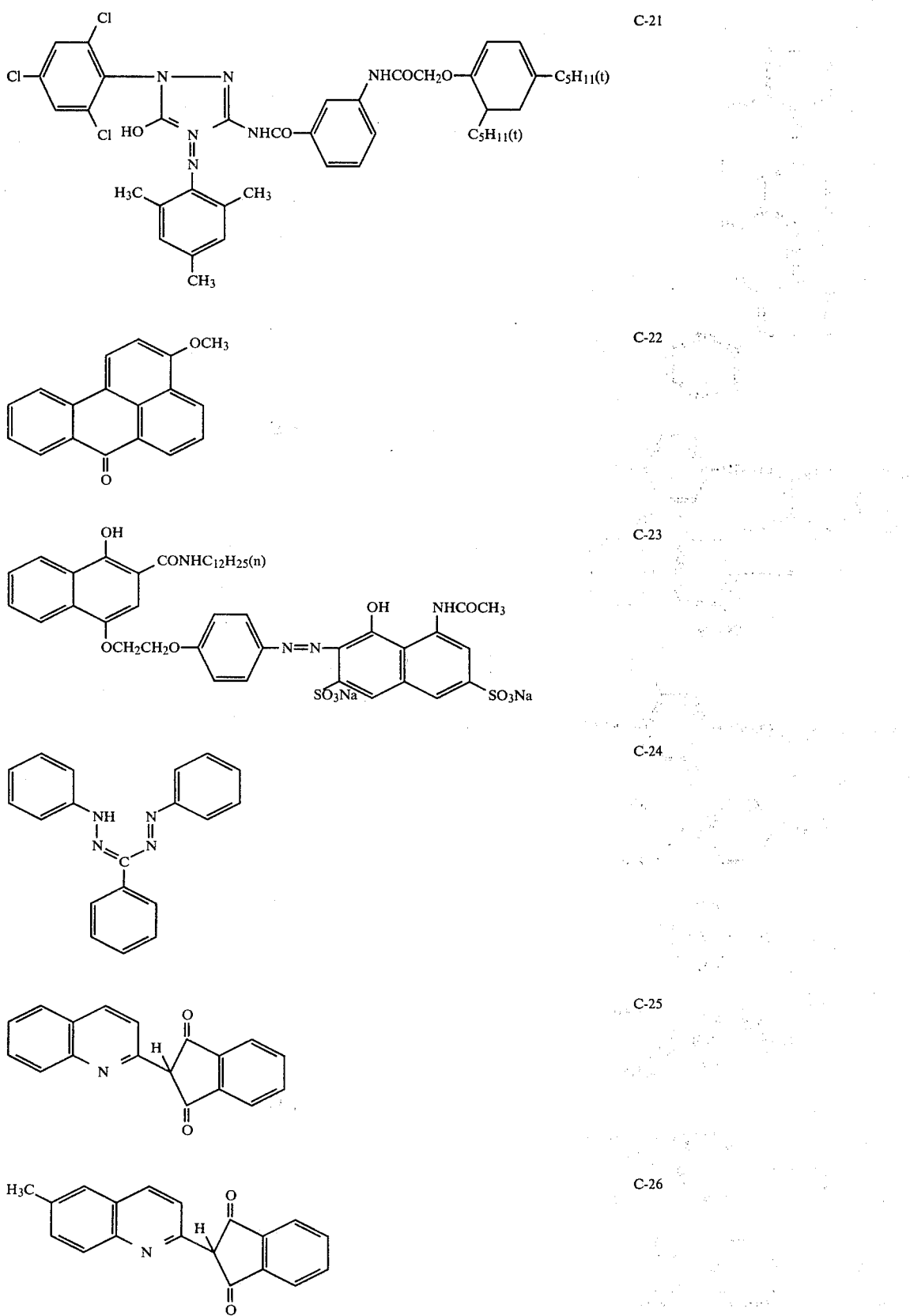

C-27
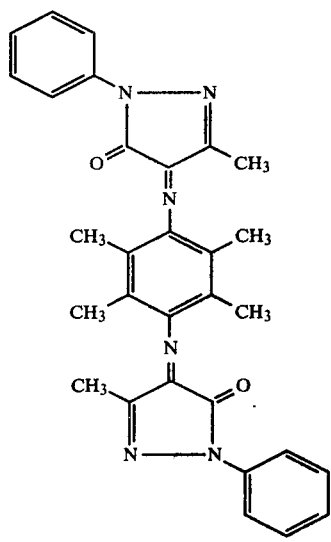
C-28
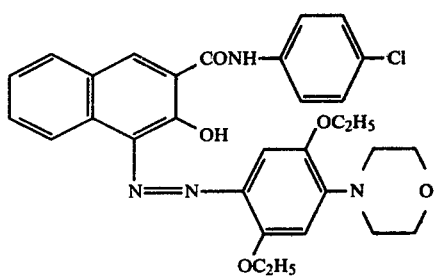
C-29
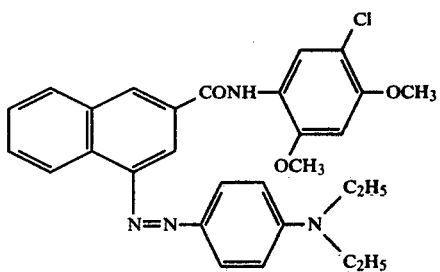
C-30
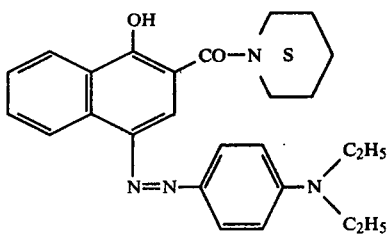
C-31
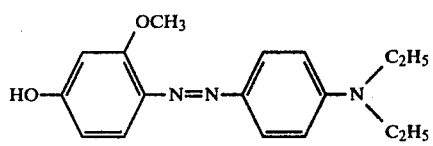
C-32
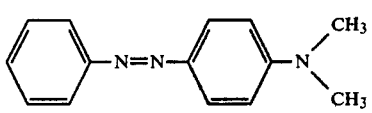

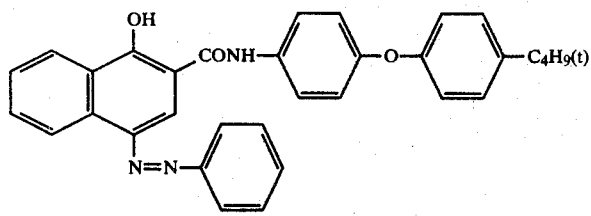 C-33
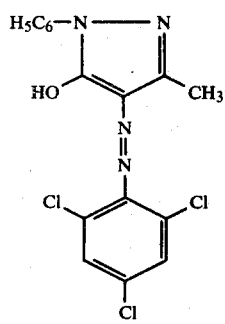 C-34
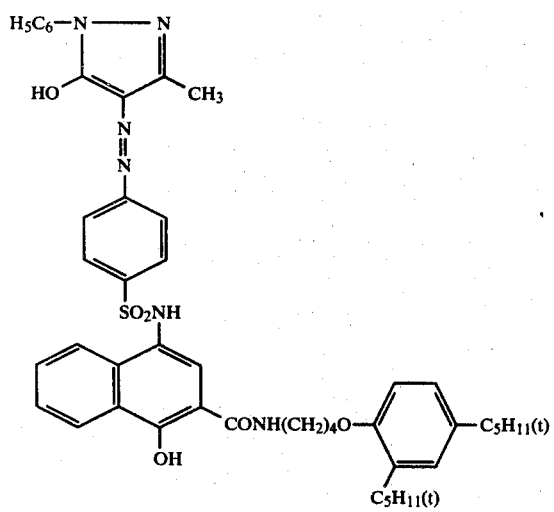 C-35
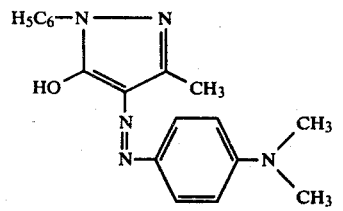 C-36
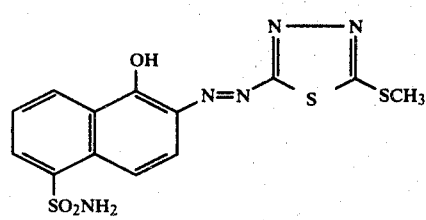 C-37
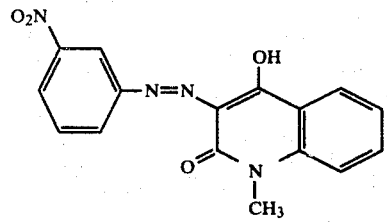 C-38

-continued
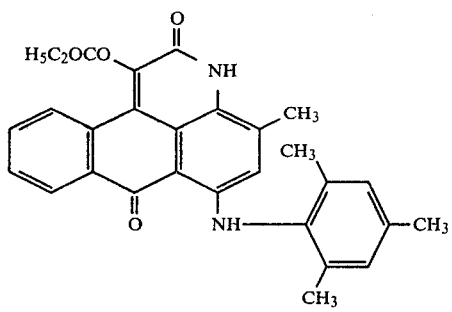 C-39
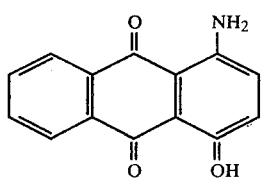 C-40
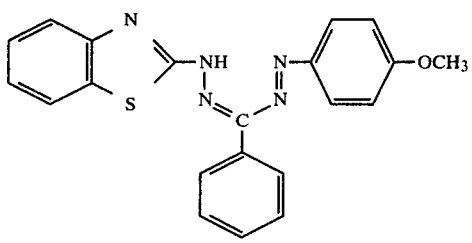 C-41
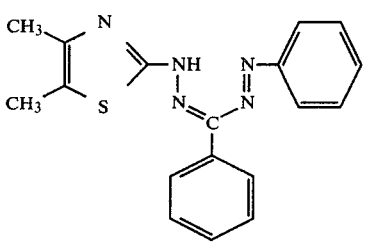 C-42
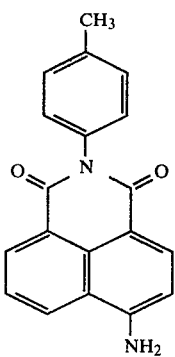 C-43
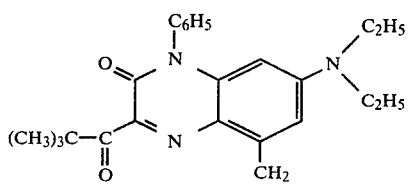 C-44
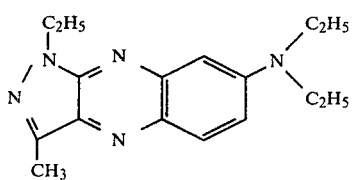 C-45

-continued
C-46
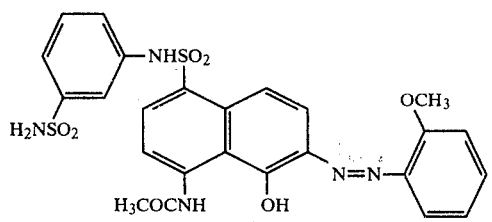
C-47
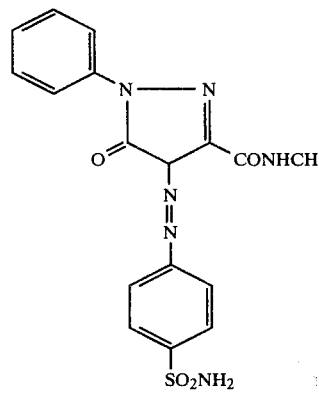
C-48
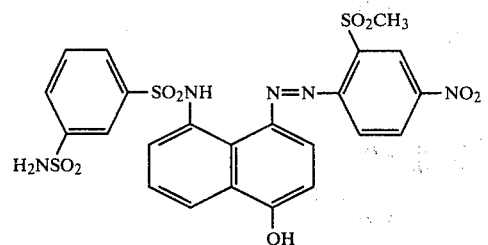
C-49
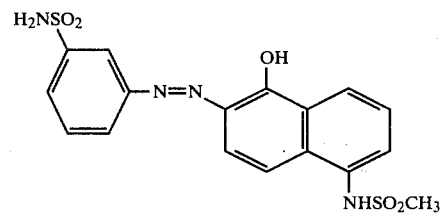
C-50
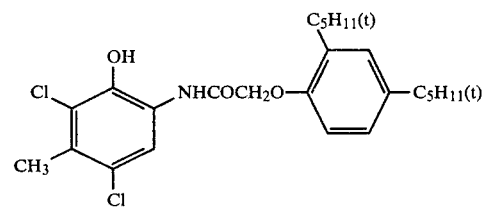
C-51
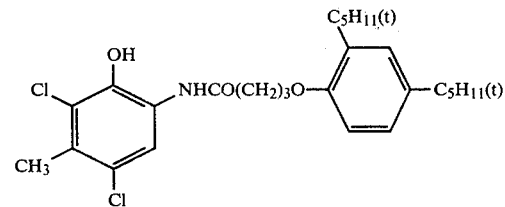
C-52
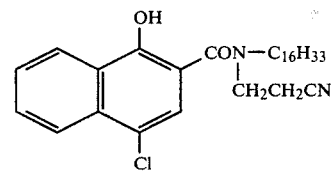

-continued
C-53
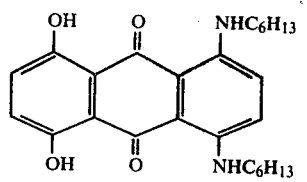
C-54
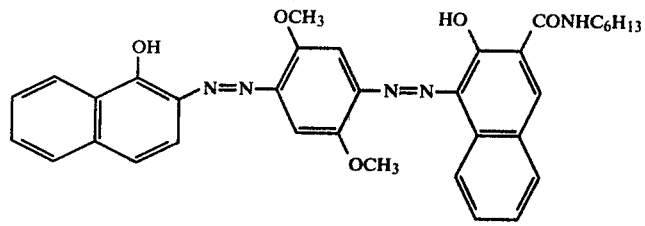
C-55
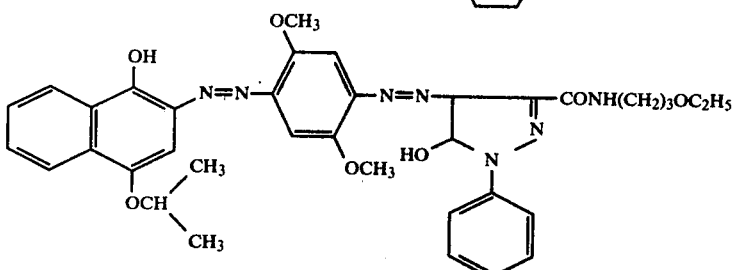
C-56
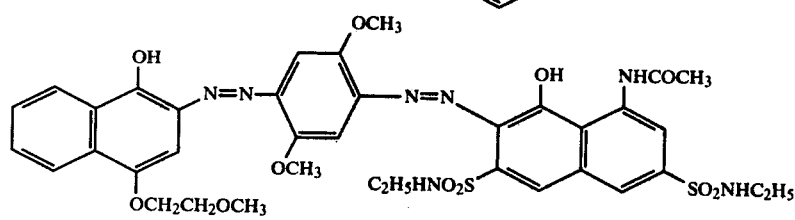
C-57
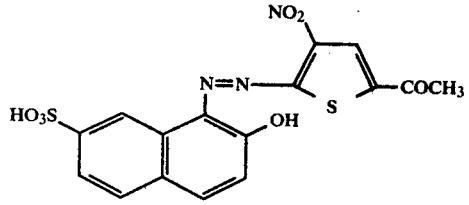
C-58
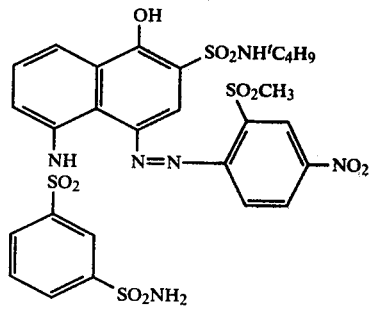
C-59
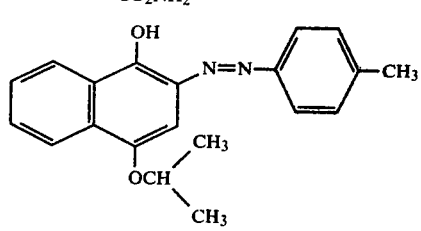
C-60
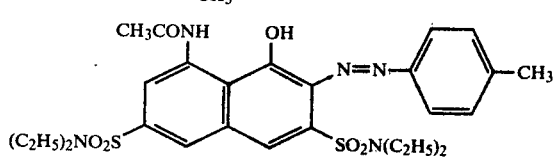

-continued
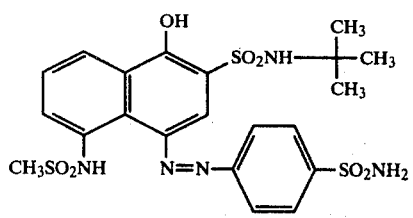
C-61
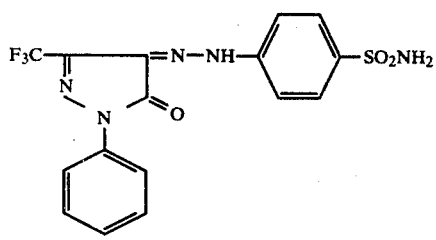
C-62
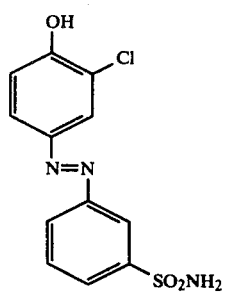
C-63
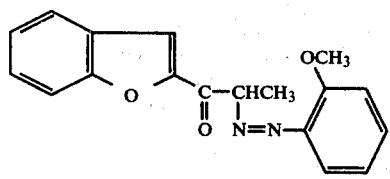
C-64
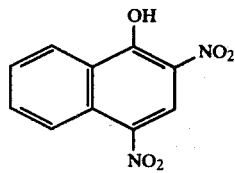
C-65
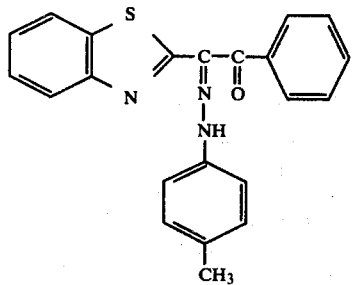
C-66
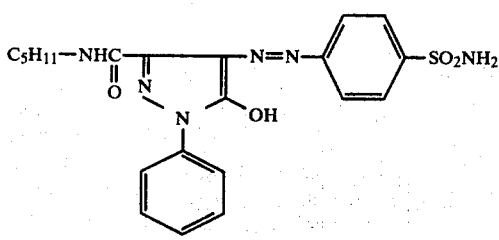
C-67

C-68

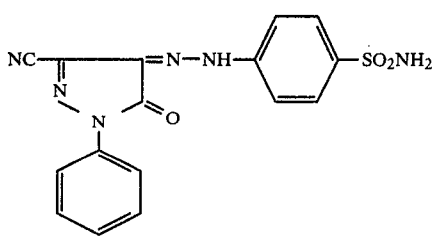

C-69

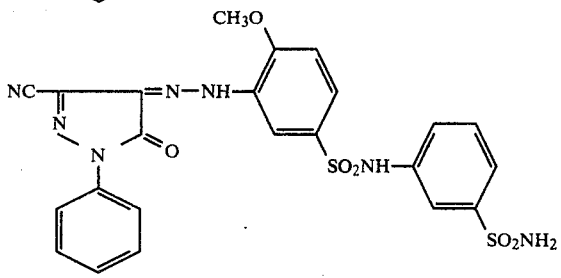

C-70

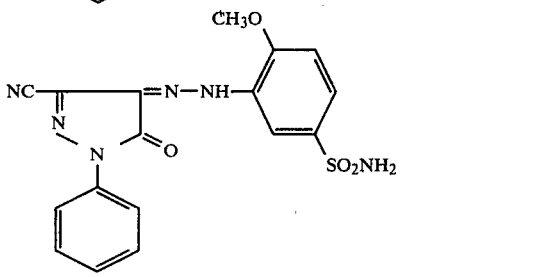

Other types of dyes preferably used in the present invention, there are illustrated dyes formed by the oxidation of DRR compounds described in U.S. Patent Publication No. B351,673, U.S. Pat. Nos. 3,932,381, 3,928,312, 3,931,144, 3,954,476, 3,929,760, 3,942,987, 3,932,380, 4,013,635, 4,013,633, Japanese Patent Application (OPI) Nos. 113,624/76, 109,928/76, 104,343/76, 4,819/77, Japanese Patent Application No. 64,533/77 corresponding to U.S. Ser. No. 911,571 (corresponding to OPI 149328/78), *Journal of Research Disclosure* (1976, Nov.), pp. 68–74, ibid., No. 13024 (1975), etc.

As the other type of dyes which may be used in the present invention, there are illustrated dyes released, upon reaction with the oxidation product of a color developing agent, from DDR couplers as described in British Pat. Nos. 840,731, 904,364, 932,272, 1,014,725, 1,038,331, 1,066,352, 1,097,064, Japanese Patent Application (OPI) No. 133,021/76, U.S. Defensive Publication T 900,029, U.S. Pat. No. 3,227,550, etc. or dyes formed by the reaction with an oxidation product of a color developing agent.

Other types of dyes preferably used in the present invention, there are illustrated by dye developers described in Japanese Patent Publication Nos. 182/60, 18,332/60, 32,130/73, 43,950/71, 2,618/74, etc.

As the other type of dyes, various dyes used in a silver dye-bleaching process may be used in the present invention. As the yellow dyes for this purpose, there are illustrated azo dyes such as Direct Fast Yellow GC (CI 29000), Chrysophenine (CI 24895), etc.; benzoquinone dyes such as Indigo Golden Yellow IGK (CI 59101), Indigosol Yellow 2GB (CI 61726), Argosol Yellow GCA-CF (CI 67301), Indanthrene Yellow GF (CI 68420), Mikethren Yellow GC (CI 67300), Indanthrene Yellow 4GK (CI 68405), etc.; anthraquinone dyes; polycyclic solubilized vat dyes; and other vat dyes. As the magenta dyes, there are illustrated azo dyes such as Sumilight Supra Rubinol B (CI 29225), Benzo Brilliant Geranin B (CI 15080), etc.; indigoid dyes such as Indigosol Brilliant Pink IR (CI 73361), Indigosol Violet 15R (CI 59321), Indigosol Red Violet IRRL (CI 59316), Indanthrene Red Violet RRK (CI 67895), Mikethren Brilliant Violet BBK (CI 6335), etc.; solubilized vat dyes comprising benzoquinone, anthraquinone or heteropolycyclic compounds, and other vat dyes. As the cyan dyes, there are illustrated azo dyes such as Direct Sky Blue 6B (CI 24410), Direct Brilliant Blue 2B (CI 22610), Sumilight Supra Blue G (CI 34200), etc.; phthalocyanine dyes such as Sumilight Supra Turquoise Blue G (CI 74180), Mikethren Brilliant Blue 4G (CI 74140), etc.; Indanthrene Turquoise Blue 5G (CI 69845), Indanthrene Blue GCD (CI 73066), Indigosol 04G (CI 73046), Anthrasol Green IB (CI 59826), etc.

While the mechanism whereby the complex of the present invention improves light fastness is not entirely clear, it is believed that upon exposure to light the organic substrate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention thereby effectively improves the light fastness of the organic substrate.

In forming a photographic product, these complexes are dissolved in solvents which do not adversely affect the photographic properties of the product. Suitable solvents are selected from low-boiling organic solvents or water-miscible solvents, such as alcohols (e.g., methanol, ethanol, isopropanol, etc.), ethers (e.g., dimethyl ether, ethyl methyl ether, diethyl ether, 1-ethoxypropane, etc.), glycols (e.g., 1,2-ethanediol, 1,2-propanediol, 1,3-propanediol, etc.), ketones (e.g., acetone, methyl ethyl ketone, 3-pentanone, etc.), esters (e.g., ethyl formate, methyl acetate, ethyl acetate, etc.), and amides (e.g., formamide, acetamide, succinic acid amide, etc.), and added as a solution to a hydrophilic colloid constituting a photographic layer to thereby stabilize the substrate. Their addition is preferably conducted before coating, for example, when preparing the silver halide photographic emulsion, when emulsifying and dispersing the couplers in the emulsion, or when preparing a photographic coating solution.

In order to add these complexes to a hydrophilic colloid constituting a photographic layer, the same techniques used in the art for dispersing couplers into such colloid layers can be employed. That is the techniques taught in U.S. Pat. Nos. 2,304,939 and 2,322,027 relying on a high-boiling organic solvent to dissolve the material may be employed. Other suitable techniques are described in U.S. Pat. Nos. 2,801,170, 2,801,171 and 2,949,360 wherein low-boiling or water-soluble organic solvents are used together with high-boiling solvents.

The high-boiling solvents effective for dispersing the substrate and the metal complex of the present invention in a hydrophillic colloid include di-n-butyl phthalate, benzyl phthalate, triphenyl phthalate, tri-o-cresyl phosphate, diphenylmono-p-tert-butylphenyl phosphate, monophenyldi-p-tert-butylphenyl phosphate, diphenylmono-o-chlorophenyl phosphate, monophenyldi-o-chlorophenyl phosphate, 2,4-di-n-amylphenol, 2,4-di-t-amylphenol, N,N-diethyllaurylamide, and trioctyl phosphate, trihexyl phosphate, etc. described in U.S. Pat. No. 3,676,137. Low-boiling or water-soluble organic solvents advantageously used together with these high-boiling solvents are disclosed in, for example, U.S. Pat. Nos. 2,801,171, 2,801,170, and 2,949,360. These organic solvents include:

(1) substantially water-insoluble organic solvents such as methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride, chloroform, etc., and (2) water-soluble organic solvents such as methyl isobutyl ketone, beta-ethoxyethyl acetate, beta-butoxytetrahydrofurfuryl adipate, diethylene glycol monoacetate, acetic acid methoxytriglycol, acetonylacetone, diacetonealcohol, ethylene glycol, diethylene glycol, dipropylene glycol, acetone, methanol, ethanol, acetonitrile, dimethylformamide, dioxane, etc.

As described above, the metal complexes of the present invention stabilize the organic substrate. In the case of a photographic material, the substrate material (the photographic dye image) and the complex each may be present in one or more of the hydrophilic colloid layers making up the photographic element (film, paper, diffusion transfer unit, etc.). It is preferred that the metal chelate complex and the organic substrate material be present (i.e., co-exist) in the same emulsion layer, of course, the effect of the present invention can also be attained when the complex and substrate are present in contiguous layers as long as diffusion is allowed to occur between the layers. That is as long as the complex can diffuse to the layer containing the dye to be stabilized. Those skilled in the art can readily determine those complexes capable of such diffusion. The complex may be located in a silver halide emulsion layer, in fact, the complex may be located in each silver halide emulsion layer making up the element in which case the total amount of complex is in the range set forth above. Where any (further) undesirable diffusion to occur, conventional mordanting techniques could be applied to the present invention. The complex may be present in non-light sensitive elements or layers as well, such as the dye image receiving layer used in diffusion transfer film units. In the case of diffusion transfer units, the metal chelate complex is preferably located in a layer where dye images are finally found, i.e., in an image-receiving layer. Usually, the dye images formed in the image-receiving layer do not diffuse further into any other layer(s) so that the complex is capable of being retained in the vicinity of the image. When the substrate and the complex are incorporated in such non light sensitive image-recording elements, they are preferably mordanted. Thus, the complex preferably possesses an organic ligand such that it is held in the mordanted layer of the image-receiving element to prevent it from diffusing from the dye to be stabilized.

A number of types of image transfer fillm units are particularly appropriate for the practice of the present invention. One is the imbibition transfer film unit set forth in U.S. Pat. No. 2,882,156. The present invention can be further used in conjunction with the color image transfer film units described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Pat. Nos. 757,959 and 757,960.

The complex and substrate used in the practice of the present invention can be used in accordance with the method described in Product Licensing Index, Vol.92 (1971, Dec.), No. 9232, pp.107-110 together with the materials described there. With respect to this point, chapters, I, II, III, IV, V, VII, VIII, IX, X, XI, XII, XIII, XIV, XV, XVI, XVII, XVIII and XXIII are pertinent.

In general, the complex of the formula (I) is dissolved or suspended in an appropriate solvent which is chosen, depending upon the physical properties of the complex used from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc. together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

Any amount of the complex will bring about some improvement in the light fastness of the organic substrate and there is no upper limit for the amount of the complex from a theoretical standpoint. Preferably, the complex is present in an amount of at least 0.1 mol% based on 1 mol of the organic substrate material, more preferably, in an amount of 0.1 to 1000 mol%, and most preferably, in an amount of 1 to 300 mol%. In the case of a photographic material, the amount is often expressed in a weight unit per square meter of photographic material which can be calculated from the parameters set out above. For convenience, however, in the case of a photographic material, the comlex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology.

As is well known to those skilled in the art, the substrate material is preferably present in the range of from about 10 to $10^3$ micromoles per square meter of the phogographic material. A more preferably range is from about 100 to about $3 \times 10^3$ micromoles per square meter of the photographic product.

The substrates used in practicing the present invention generally have a maximum wavelength absorption peak in the range shorter than about 800 nm. The maximum wavelength absorption peak of the base material preferably exists in the range of from about 300 to about 800 nm, most preferably from about 400 nm to about 800 nm.

In the photographic light-sensitive material used in conjunction with the present invention, any support that is typically used as the support for ordinary photographic light-sensitive materials can be used. For example, there are a cellulose nitrate film, a cellulose acetate film, a cellulose acetate butyrate film, a cellulose acetate propionate film, a polystyrene film, a polyethylene terephthalate film, a polycarbonate film, laminates thereof, paper, etc. In addition, papers having coated or laminated thereon baryta or an olefin polymer, in particular a polymer of α-olefin containing 2–10 carbon atoms such as polyethylene, polypropylene, etc. and plastic films whose surface has been made rough to improve an intimate property with other high molecular materials as described in Japanese Patent Publication No. 19,068/72 are also preferred.

Various hydrophilic colloids are used for the photographic light-sensitive material in the method of the present invention. As the hydrophilic colloid used as a binder for making up the photographic emulsions and/or other photographic layers, there are illustrated, for example, gelatin, colloidal albumin, casein, cellulose derivatives (e.g., carboxymethyl cellulose, hydroxyethyl cellulose, etc.), sugar derivatives (e.g., agar-agar, sodium alginate, starch derivative, etc.), synthetic hydrophilic colloids (e.g., polyvinyl alcohol, poly-N-vinyl pyrrolidone, polyacrylic acid copolymer, maleic anhydride copolymer, polyacrylamide, or the derivative or partly hydrolyzed product thereof), etc. If necessary, a compatible mixture of two or more of these colloids is used.

Of these colloids, gelatin is most commonly used. Gelatin can be replaced, partially or wholly, by a synthetic high molecular weight substance, by a so-called gelatin derivative [prepared by processing and modifying gelatin with a reagent having a group capable of reacting with the functional groups contained in the gelatin molecule (i.e., amino groups, imino groups, hydroxy groups or carboxy groups)], or by a graft polymer prepared by grafting a molecular chain of another high molecular substance.

Synthetic polymer compounds such as latex-like vinyl compound polymer dispersed in water, compounds capable of increasing, in particular, the dimensional stability of photographic materials, and the like, alone or in combination with other polymers or in combination with a hydrophilic, water-permeable colloid may be used in the photographic emulsion layers and other layers.

The silver halide photographic emulsion is usually prepared by mixing a solution of water-soluble silver salt (e.g., silver nitrate, etc.) with a solution of water-soluble halide (e.g., potassium bromide) in the presence of a solution of a water-soluble high polymer such as gelatin. As the silver halide, mixed silver halides such as silver chlorobromide, silver bromoiodide, silver chlorobromoiodide, etc. can be used as well as silver chloride and silver bromide. These silver halide grains are prepared according to known conventional processes. Of course, they are easily prepared by a so-called single- or double-jet process, controlled double jet process, or the like. Also, two or more silver halide photographic emulsions separately prepared may be mixed to use.

Various compounds for preventing reduction in sensitivity or formation of fog in the steps of producing light-sensitive materials, during storage or during photographic processings may be added to the above-described photographic emulsion. As such compounds, there have long been known many compounds such as many heterocyclic compounds including 4-hydroxy-6-methyl-1,3,3a-7-tetrazaindene, 3-methylbenzothiazole and 1-phenyl-5-mercaptotetrazole, mercury-containing compounds, mercapto compounds, metal salts, and the like.

The silver halide emulsion used in the method of the present invention can be chemically sensitized in a conventional manner. Illustrative chemically sensitizing agents are, for example, gold compounds such as chloroauric acid salt, auric chloride, salts of noble metals such as platinum, palladium, iridium, rhodium, ruthenium, etc., sulfur compounds capable of reacting with a silver salt to form silver sulfide, stannous salts, amines and other reducing substrates.

The photographic emulsions may, if necessary, be subjected to spectral sensitization or supersensitization using cyanine dyes such as cyanine, merocyanine, carbocyanine, etc. alone or in combination, or in further combination with styryl dyes, etc. They can be optionally selected according to the wavelength region to be sensitized, end-use of the light-sensitive material like sensitivity, etc.

The hydrophilic colloidal layer of the light-sensitive material to be used in the method of the present invention may be hardened, if necessary, with various cross-linking agents. For example, they can be selected from among aldehyde compounds, active halogen compounds, vinyl-sulfone compounds, carbodiimide compounds, N-methylol compounds, epoxy compounds, etc.

In one embodiment a color photographic light-sensitive material treated in accordance with the method of the present invention is processed, after imagewise exposure, in a conventional manner. The main processing steps in this case are color developing, bleaching and fixing and, if necessary, washing and the like may be involved. Two or more steps may be conducted in one bath, such as, bleach-fixing. Color development is usually conducted in an alkaline solution containing an aromatic primary amine developing agent.

Preferred specific examples of the aromatic primary amine developing agents are the compounds of structural formulae (A)–(L) described above.

In another embodiment the color photographic light-sensitive material is automatically conducted inside the light-sensitive material where the light-sensitive material is a color diffusion transfer film unit. In this case, the developing agent is retained in a rupturable container. As the developing agent, there may be used N-methylaminophenol, 1-phenyl-3-pyrazolidone, 1-phenyl-4,4-dimethyl-3-pyrazolidone, 1-phenyl-4-methylhydroxymethyl-3-pyrazolidone, 3-methoxy-N,N-diethyl-p-phenylendiamine, etc. as well as the above-described compounds (A)–(L).

In order to form a color image in the photographic light-sensitive material used in the present invention, there may be employed known processes such as a process of utilizing coupling reaction between the aforesaid dye-forming color coupler and an oxidation product of a color developing agent, a process of using a dye developer, a process of utilizing an oxidative cleavage reaction of a DRR coupler compound, a process of utilizing the dye elimination reaction of a DDR coupler through coupling reaction, a process of utilizing a dye-forming reaction, or a process of using silver dye-bleaching techniques as explained above.

In summary, the present invention can be applied to various color photographic light-sensitive material such as color positive film, color paper, color negative film, color reversal film, color diffusion transfer film unit, light-sensitive material for use in silver dye-bleaching, etc.

EXAMPLE 1

0.1 g of 1-(2,4,6-trichlorophenyl)-3-(2-chloro-5-tetradecanamido)anilino-4-[4-(N-ethyl-N-beta-methanesulfonamidoethyl)aminophenylimino]-5-oxo-2-pyrazolone was dissolved in 3 ml of tricresyl phosphate and 5 ml of ethyl acetate, and the resulting solution was emulsified and dispersed in 10 g of 10% gelatin containing 1 cc of a 1% sodium dodecylbenzenesulfonate aqueous solution. Then, this emulsion dispersion was mixed with 10 g of 10% gelatin and coated on a paper support laminated on both sides with polyethylene, followed by drying to prepare sample A. The dye was coated in an amount of 60 mg/m$^2$.

In the same manner as described above, sample B was prepared by adding 30 mg of compound I-11 of the present invention upon preparation of the above-described emulsion dispersion and coating in the same manner in a coating amount of 18 mg/m$^2$ as with sample A. Samples C and D were prepared by adding a conventional fade preventing agent, 2,5-di-tert-octylhydroquinone, in amounts of 10 mg and 100 mg, respectively, and coating in the same manner as with sample A.

Samples A–D were subjected to a fading test for 36 hours using a xenon tester (made by Fuji Photo Film Co., Ltd.) having an illuminance of 200,000 lux fitted with an ultraviolet ray-cutting filter, C-40.

The results are shown in Table below.

Table 1

| Sample | Initial Density | Density after 36 hrs |
|--------|-----------------|----------------------|
| A      | 0.79            | 0.03                 |
| B      | 0.81            | 0.73                 |
| C      | 0.81            | 0.09                 |
| D      | 0.82            | 0.38                 |

The density measurement was conducted using a Macbeth densitometer, model RD514, and a green filter of AA status. Sample B containing compound I-11 of the present invention suffered extremely less fading in comparison to samples A, C and D. In particular, samples C and D, the fading-preventing effect of 2,5-di-tert-octylhydroquinone was confirmed to be extremely small though it was contained in an equimolar amount to, or 10 times as much as, that of compound I-11 of the present invention. This shows that compound I-11 of the present invention shows a remarkable fade preventing effect.

EXAMPLE 2

0.1 g of compound C-23 was dissolved in 0.2 cc of 1 N-NaOH and 2 cc of methanol, and this solution was added to 10 g of 10% gelatin. This solution was coated in an amount of 80 mg of compound C-23/m$^2$ on a paper support laminated on both sides with polyethylene to prepare sample E.

In the same manner as for Sample E described above, sample F was prepared by adding a solution prepared by dissolving 200 mg of compound I-12 of the present invention in 2 cc of methanol to the solution of C-23 immediately before coating and then coating in the same manner as with sample E in an amount of 160 mg (I-12)/m$^2$. Sample G was prepared as a comparative sample by adding 100 mg of a conventional fade prevention of α-tocopherol and coating in the same manner. These samples were subjected to the fading test for 12 hours using a xenon tester fitted with an ultraviolet ray-absorbing filter in the same manner as in Example 1.

The results are shown in Table II.

Table II

| Sample | Initial Density | Density after 12 hrs |
|--------|-----------------|----------------------|
| E      | 0.90            | 0.05                 |
| F      | 0.91            | 0.60                 |
| G      | 0.91            | 0.13                 |

The measurement was conducted in the same manner as in Example 1 using a Macbeth densitometer. It is seen from this table that the light fastness obtained with compound I-12 of the present invention is extremely great.

EXAMPLE 3

10 g of a magenta coupler, 1-(2,4,6-trichlorophenyl)-3-[(2-chloro-5-tetradecanamido)anilino]-2-pyrazolin-5-one, was dissolved in 30 ml of trioctyl phosphate, 5 ml of dimethylformamide and 15 ml of ethyl acetate, and the resulting solution was emulsified and dispersed in 80 g of a 10% gelatin solution containing 8 cc of a 1% sodium dodecylbenzenesulfonate aqueous solution. This emulsion dispersion was mixed with 145 g (containing 7 g of Ag) of a green-sensitive silver bromochloride emulsion (Br: 50 mol%), and 3 cc of a 1% sodium dodecylbenzenesulfonate aqueous solution was added thereto as a coating aid. The resulting solution was coated on a paper support laminated on both sides with polyethylene to obtain sample H. The coating amount of the coupler was 400 mg/m².

In the same manner as described above, sample I was prepared by adding 0.5 g of compound I-30 of the present invention upon preparation of the above-described emulsion dispersion and coating in the same manner as with sample H to provide a coating amount for compound I-30 of 20 mg/m². Sample J was prepared by adding 2.0 g of 2,2'-methylenebis-(4-methyl-6-tert-butylphenol), a known fade prevention agent and coating in the same manner as with Sample H.

These samples were exposed for 1 second to a tungsten lamp with an illuminance of 1,000 lux, and possessed with the following processing solutions.

| Developer | |
|---|---|
| Benzyl alcohol | 15 ml |
| Diethylenetriaminepentaacetic acid | 5 g |
| KBr | 0.4 g |
| Na₂SO₃ | 5 g |
| Na₂CO₃ | 30 g |
| Hydroxyamine sulfate | 2 g |
| 4-Amino-3-methyl-N-ethyl-N-beta-(methanesulfonamido)ethylaniline . 3/2H₂SO₄·H₂O | 4.5 g |
| Water to make | 1,000 ml |
| Bleach-fixing solution | |
| Ammonium thiosulfate (70 wt %) | 150 ml |
| Na₂SO₃ | 5 g |
| Na[Fe(EDTA)] | 40 g |
| EDTA | 4 g |
| Water to make | 1,000 ml |
| | (pH = 6.8) |

Processing steps

| | Temperature | Time |
|---|---|---|
| Developer | 33° C. | 3½ min. |
| Bleach-fixing solution | 33° C. | 1½ min. |
| Washing with water | 28°-35° C. | 3 min. |

Each sample on which an dye image had been formed as above was subjected to a fading test for 4 weeks using a fluorescent lamp fading tester (20,000 lux) fitted with an ultraviolet ray-absorbing filter, C-40, made by Fuji Photo Film Co., Ltd. for cutting light of not longer than 400 nm.

The results are shown in Table III. The measurement was conducted using Macbeth densitometer, RD-154 (status AA filter) to measure the change in the density in an area with an initial density of 2.0.

Table III

| Sample | Density after the fading test | Dye-surviving ratio* |
|---|---|---|
| H | 0.48 | 24% |
| I | 1.85 | 92.5% |

Table III-continued

| Sample | Density after the fading test | Dye-surviving ratio* |
|---|---|---|
| J | 1.26 | 63% |

*Dye-surviving ratio = $\frac{\text{Density after fading}}{2.0} \times 100$

The above results show that compound I-30 of the present invention is an effective fading-preventing agent.

EXAMPLE 4

A solution of 50 mg of a dye having the structure below and 500 mg of polycarbonate Lexan 145 (tradename, manufactured by General Electric Co.) in 100 ml of dichloromethane was coated onto a glass plate using a spinner. A magenta-colored film of 5.5 μm was thus prepared as Sample K.

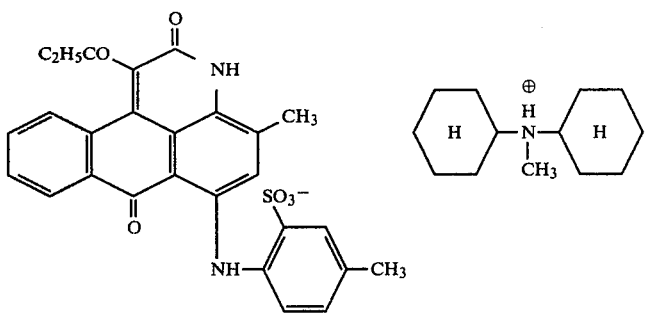

In a similar manner, five kinds of colored films were prepared as Samples L, M, N, O and P except that Compounds I-4, I-26, I-27, I-28 and I-29 were further incorporated into the solution, respectively.

The coating rates of the dye and the fade prevention compounds were 500 mg/m² and 50 mg/m², respectively.

The thus obtained films were exposed to sunlight for one month and a color fading test was carried out.

The results obtained are shown in Table IV, in which the density was measured at 550 nm.

Table IV

| Sample | Initial Density | Density After Fading |
|---|---|---|
| K | 1.0 | 0.55 |
| L | 1.0 | 0.90 |
| M | 1.0 | 0.88 |
| N | 1.0 | 0.80 |
| O | 1.0 | 0.90 |
| P | 1.0 | 0.65 |

It can be clearly understood from the results shown in the foregoing table that the system of the instant invention, particularly Samples L and O, showed only a 10% reduction in density after the one month color fading, whereas the density of the system where no chelate complex was present was reduced 55%. That is, the system of the instant invention exhibits superior light fastness to Sample K.

Briefly summarizing the effects achieved by the metal chelate complex employed in the present invention:

(1) The metal chelate complex is readily soluble in organic solvents.

(2) In addition, the structure of the chelate complex can easily be modified so that it permits a large latitude for obtaining desired solubility.

(3) As a result of the latitude of its solubility, the complex is readily enveloped in oild droplets and as a result, photographically undesired interaction with silver halide (e.g., desensitization) is avoidable.

(4) Due to its extremely high solubility, a small amount of the complex is sufficient to effect light fastness; conversely, a large amount can also be employed as in the case of umbrellas, agricultural vinyl cover sheets, etc.

(5) Where the chelate is used in a photographic element, no adverse effect on photographic properties is encountered.

(6) The complex is the first fading preventing agent suitable for improving the light fastness of cyan dye images.

For the reasons above, the metal chelate complex used in the present invention provides excellent light fastness.

While the invention has been described in detail and with reference to specific embodiments thereof, it will be apparent to one skilled in the art that various changes and modifications can be made therein without departing from the spirit and scope thereof.

What is claimed is:

1. A method for stabilizing a photographically useful organic substrate selected from the group consisting of a quinoneimine dye, a methine or polymethine dye, an azo dye, an anthraquinone dye, an indoamine or indophenol dye, an indigoid dye, a carbonium dye, and a formazan dye to light said substrate having an absorption maximum in the range of about 300 nm-about 800 nm, which comprises making at least one complex in an amount sufficient to stabilize said color photographic material to light represented by following general formula (I) coexist with said substrate:

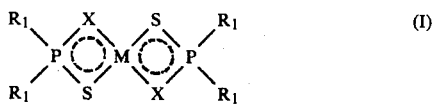

wherein M represents an atom selected from the group consisting of Cu, Co, Ni, Pd and Pt, X represents O or S, $R_1$ represents an alkyl group, an aryl group, an alkoxy group, an aryloxy group or, when taken together, the $R_1$'s bound to the same phosphorus atom represent the non-metallic atoms necessary to complete a 6-membered ring together with the phosphorus atom.

2. The method of claim 1, wherein said compound is represented by the formula (Ia)

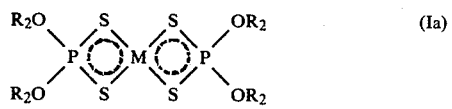

wherein M represents an atom selected from the group consisting of Cu, Co, Ni, Pd and Pt, and $R_2$ represents an alkyl group containing 1 to 20 carbon atoms or an aryl group containing 6 to 14 carbon atoms.

3. The method of claims 1 or 2 wherein said organic substrate is a photographic dye image.

4. The method of claim 1, wherein $R_1$ represents a substituted or unsubstituted, straight or branched chain alkyl group having 1 to 20 carbon atoms, a substituted or unsubstituted monocyclic or bicyclic aryl group having 6 to 14 carbon atoms, a substituted or unsubstituted alkoxy group, the alkyl moiety of which may be straight, branched or cyclic and contains 1 to 20 carbon atoms or a substituted or unsubstituted monocyclic or bicyclic aryloxy group containing 6 to 14 carbon atoms.

5. The method of claim 2, wherein said alkyl group is selected from the group consisting of methyl, ethyl, n-propyl, iso-propyl, n-butyl, n-amyl, iso-amyl, n-decyl, and n-octadenyl and said aryl group is phenyl or naphthyl.

6. The method of claim 3, wherein said photographic dye image is formed upon the reaction of the oxidation product of a color developing agent and a color coupler.

7. The method of claim 3, wherein said photographic dye image is formed by imagewise oxidation of a DRR compound.

8. The method of claim 3, wherein said photographic dye image is the image of a dye used in a silver dye-bleaching process.

9. The method of claim 3, wherein said dye image is formed by the coupling reaction of a DDR coupler.

10. The method of claim 3, wherein said photographic dye has an absorption maximum at about 300 to about 800 nm.

11. The method of claim 6, wherein said coupler is a cyan, magenta or yellow coupler.

12. A color photographic material comprising at least one layer containing a photographic dye image wherein said layer or an adjacent layer contains a compound of the formula (I) in an amount sufficient to stabilize said color photographic dye image to light

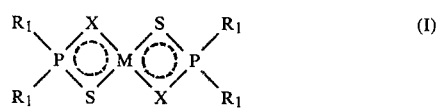

wherein M represents an atom selected from the group consisting of Cu, Co, Ni, Pd and Pt, X represents O or S, $R_1$ represents an alkyl group, an aryl group, an alkoxy group, an aryloxy group or, when taken together, the $R_1$'s bound to the same phosphorus atom represents the non-metallic atoms necessary to complete a 6-membered ring together with the phosphorus atom.

13. The color photographic material of claim 12 wherein said compound is represented by the formula (Ia)

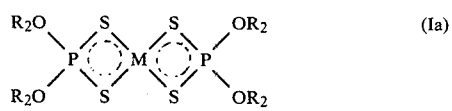

wherein M represents an atom selected from the group consisting of Cu, Co, Ni, Pd and Pt, and $R_2$ represents an alkyl group containing 1 to 20 carbon atoms or an aryl group containing 6 to 14 carbon atoms.

14. The color photographic material of claim 12 wherein said dye image has an absorption maximum at about 300 to about 800 nm.

15. The color photographic material of claim 12 wherein said dye image is a quinoneimine dye, a methine or polymethine dye, an azo dye, an anthraquinone dye, an indoamine or indophenol dye, an indigoid dye, a carbonium dye, or a formazan dye.

16. The color photographic material of claim 12 wherein said dye image is formed upon the reaction of the oxidation product of a color developing agent and a color coupler.

17. The photographic color material of claim 12 wherein said dye image is formed by imagewise oxidation of a DRR compound.

18. The photographic color material of claim 12 wherein said dye image is the image of a dye used in a silver dye-bleaching process.

19. The photographic color material of claim 12 wherein said dye image is formed by the coupling reaction of a DDR coupler.

20. The photographic color material of claim 16 wherein said coupler is a cyan, magenta or yellow coupler.

21. A diffusion transfer color photographic material comprising a photosensitive element and an image receiving element said image receiving element comprising a support having thereon a mordanting layer containing a complex of the formula (I) in an amount sufficient to stabilize said diffusion transfer color photographic material to light

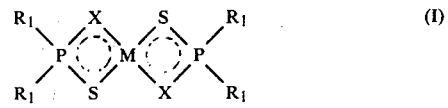

wherein M represents an atom selected from the group consisting of Cu, Co, Ni, Pd and Pt, X represents O or S, $R_1$ represents an alkyl group, an aryl group, an alkoxy group, an aryloxy group or, when taken together, the $R_1$'s bound to the same phosphorus atom represent the non-metallic atoms necessary to complete a 6-membered ring together with the phosphorus atom.

22. The method of claim 1 wherein said substrate is a color dye forming a color photographic image.

23. The color photographic material of claim 12 wherein said compound of the formula (I) is present in an amount sufficient to prevent color fading.

* * * * *